United States Patent
Dubois et al.

(10) Patent No.: US 8,212,070 B2
(45) Date of Patent: Jul. 3, 2012

(54) METHOD FOR PREPARING ACRYLIC ACID FROM GLYCEROL

(75) Inventors: Jean-Luc Dubois, Millery (FR); Greégory Patience, Ville Mont-Royal (CA)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 12/520,073

(22) PCT Filed: Dec. 14, 2007

(86) PCT No.: PCT/FR2007/052526
§ 371 (c)(1),
(2), (4) Date: Jan. 14, 2010

(87) PCT Pub. No.: WO2008/087315
PCT Pub. Date: Jul. 24, 2008

(65) Prior Publication Data
US 2010/0168471 A1    Jul. 1, 2010

(30) Foreign Application Priority Data
Dec. 19, 2006  (FR) ...................................... 06 55636

(51) Int. Cl.
*C07C 51/235*  (2006.01)
(52) U.S. Cl. ........................................ 562/532; 562/545
(58) Field of Classification Search .................. 562/532, 562/545
See application file for complete search history.

(56) References Cited

U.S. PATENT DOCUMENTS

| | | | |
|---|---|---|---|
| 5,387,720 A | 2/1995 | Neher et al. | |
| 7,396,962 B1 * | 7/2008 | Dubois et al. | 568/485 |
| 2005/0020851 A1 | 1/2005 | Olbert et al. | |
| 2008/0183013 A1 * | 7/2008 | Dubois et al. | 562/538 |

FOREIGN PATENT DOCUMENTS

| | | |
|---|---|---|
| DE | 2005026624 | 12/2006 |
| EP | 0995491 A1 | 9/1999 |
| EP | 1147807 A2 | 3/2001 |
| EP | 1710227 A1 | 1/2005 |
| WO | WO 2006/092272 | 9/2006 |
| WO | WO 2006/114506 | 11/2006 |
| WO | WO 2006136336 A2 | 12/2006 |

OTHER PUBLICATIONS

Tanabe, et al: "Studies in Surface Science and Catalysis", vol. 51, 1989, Chapters 1 and 2.
Marcilly; Publication on acid-bass catalysis; vol. 1; Editions Technip: ISBN No. 2-7106-0841-2, 2003.

* cited by examiner

*Primary Examiner* — Taylor Victor Oh
(74) *Attorney, Agent, or Firm* — Hunton & Williams, LLP

(57) ABSTRACT

The invention relates to a method for preparing acrylic acid from an aqueous glycerol solution, comprising a first step of dehydration of the glycerol to acrolein, carried out in the gas phase in the presence of a catalyst and under a pressure of between 1 and 5 bar, and a second step of oxidation of the acrolein to acrylic acid, in which an intermediate step is implemented, consisting in at least partly condensing the water and heavy by-products present in the stream issuing from the first dehydration step. This method serves to obtain high acrylic acid productivity and selectivity.

7 Claims, 2 Drawing Sheets

METHOD FOR PREPARING ACRYLIC ACID FROM GLYCEROL

CROSS-REFERENCE TO RELATED APPLICATIONS

This application is the U.S. National Phase Application of International Application No. PCT/FR2007/052526, filed Dec. 14, 2007, which claims the benefit of French Application No. FR 0655636, filed Dec. 19, 2006, the disclosures of which is incorporated herein by reference in their entirety.

FIELD OF THE INVENTION

The present invention relates to an improved method for preparing acrylic acid from glycerol, comprising a first step of dehydration of the glycerol to acrolein and a second step of oxidation of the acrolein to acrylic acid, in which an intermediate step of partial condensation of the water and heavy by-products issuing from the dehydration step is implemented.

BACKGROUND

Glycerol (also called glycerine) is produced by the methanolysis of vegetable oils at the same time as the methyl esters which are employed in particular as motor fuels or fuels in diesel and home-heating oil. It is a natural product, available in large quantities, and can be stored and transported without difficulty. It has the advantage of being a renewable raw material meeting the criteria associated with the new concept of "green chemistry". The development of glycerol has attracted considerable research, and the preparation of acrylic acid is one of the alternatives considered.

Application WO 06/114506 describes a method for preparing acrylic acid in one step by the oxydehydration reaction of glycerol in the presence of molecular oxygen. The principle of the method is based on the two consecutive dehydration and oxidation reactions:

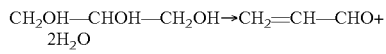

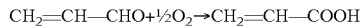

The presence of oxygen serves to carry out an oxidation reaction, following the glycerol dehydration reaction, leading to the formation of acrylic acid from the glycerol in a single step. This method can be implemented in the gas phase or the liquid phase, with concentrated or dilute aqueous solutions of glycerol. This method for producing acrylic acid directly from glycerol is particularly advantageous because it allows synthesis in a single reactor. However, it is necessary to introduce all the molecular oxygen from the dehydration stage. This has many drawbacks, in particular the reaction in the first dehydration step risks running out of control by combustion, and furthermore, when the source of molecular oxygen is air, the reactor must be much larger because of the presence of nitrogen in the air.

In patent application EP 1 710 227, the reaction product resulting from the gas phase glycerol dehydration reaction is subjected to a subsequent gas phase oxidation step to obtain acrylic acid. The method is implemented in two reactors in series, each comprising a catalyst suitable for the reaction carried out. It is recommended to add oxygen to the gas mixture fed to the second reactor, in order to improve the oxidation reaction and to obtain acrylic acid with a high yield. This two-step method is implemented with pure glycerol or with aqueous solutions comprising more than 50% by weight of glycerol. It is recommended to use a concentrated glycerol solution in order to limit the energy cost associated with the evaporation of the aqueous solution and the cost incurred by wastewater treatment. However, if the glycerol concentration is too high, more undesirable reactions are liable to occur, like the formation of glycerol ethers, or reactions between the acrolein or acrylic acid produced and the glycerol.

International application WO 2006/092272 describes a method for preparing acrylic acid from glycerol comprising either a liquid-phase glycerol dehydration step, or a gas-phase dehydration step. According to example 1, the gaseous reaction mixture containing the acrolein obtained from the gas phase glycerol dehydration reaction is contacted with water in a quench unit before being sent to the oxidation reactor.

In the method for preparing acrylic acid from glycerol described in international application WO 2006/136336, the aqueous stream leaving the dehydration reactor is treated in order to recycle to the reactor an acrolein-depleted phase containing the unreacted glycerol and to supply the oxidation reactor with an acrolein-enriched phase. The dehydration reaction is carried out at high pressure, particularly at a pressure above 50 bar, using very dilute aqueous solutions of glycerol, in particular containing less than 10% by weight of glycerol.

The use of an aqueous solution of glycerol in a two-step method has the drawback of producing, at the outlet of the first stage, a stream containing not only the acrolein produced and the by-products, but also a large quantity of water, originating partly from the glycerol solution, and partly from the water produced by the dehydration reaction. This stream is sent to the second reactor, where the acrolein is oxidized to acrylic acid in the presence of a catalyst. The conventional catalysts for this oxidation reaction are generally solids containing at least one element selected from Mo, V, W, Re, Cr, Mn, Fe, Co, Ni, Cu, Zn, Sn, Te, Sb, Bi, Pt, Pd, Ru, Rh, present in metal form or oxide, nitrate, carbonate, sulphate or phosphate form. Certain elements, such as molybdenum, tellurium or rhenium, are volatile, particularly in the presence of water. This means that the second stage catalyst loses its efficiency and its mechanical strength rapidly in the presence of the stream of water, making the maintenance of the method difficult. Moreover, the acrylic acid, produced in a dilute aqueous solution, requires separation and concentration steps which are generally complicated and fairly costly.

However, it has been surprisingly found that the presence of water in the dehydration reactor serves to promote the gas phase glycerol dehydration reaction by limiting the deactivation of the dehydration catalyst.

SUMMARY OF THE INVENTION

According to the present invention, an improved method is proposed for synthesizing acrylic acid from glycerol, which overcomes the drawbacks of the abovementioned methods, while allowing the use of dilute aqueous solutions of glycerol which enhance the dehydration reaction while being economical.

The solution provided by the invention constitutes an optimization between the quantity of water fed to the first stage dehydration reactor and the quantity of water introduced into the second stage oxidation reactor. The solution consists in at least partly condensing the water present in the stream issuing from the dehydration reaction of the aqueous glycerol solution, to prevent the second stage catalyst from being deactivated too rapidly, on the one hand, and to prevent the acrylic acid solution produced from being too dilute, on the other.

DETAILED DESCRIPTION OF PREFERRED EMBODIMENTS

More precisely, the present invention relates to a method for preparing acrylic acid from an aqueous solution of glycerol, comprising a first step of dehydration of the glycerol to acrolein, carried out in the gas phase in the presence of a catalyst and under a pressure of between 1 and 5 bar, and a second step of oxidation of the acrolein to acrylic acid, in which an intermediate step, consisting in at least partly condensing the water and heavy by-products present in the stream issuing from the first dehydration step is implemented.

In the method according to the invention, the expression at least partly condensing means that 20% to 95%, preferably 40% to 90%, of the water present in the stream issuing from the first step is removed in the intermediate step before being sent to the second stage reactor.

The dehydration reaction of glycerol to acrolein is generally accompanied by side reactions giving rise to the formation of by-products, such as hydroxypropanone, propanaldehyde, acetaldehyde, acetone, phenol, acrolein to glycerol addition products, glycerol polycondensation products, and cyclic glycerol ethers. The intermediate condensation of the method of the invention also has the advantage of at least partly separating the heavy by-products produced by these side reactions. This improves the selectivity of the oxidation reaction, which takes place in the absence of these by-products.

Other features and advantages of the invention will appear more clearly from a reading of the description that follows and with reference to the appended figure, which schematically shows one embodiment of the invention.

In the method of the invention, use is made of an aqueous glycerol solution having a concentration of between 20% and 99% by weight in the reactor, preferably between 30% and 80%.

The glycerol solution can be used in liquid form or in gas form, preferably in gas form.

Figure 1:
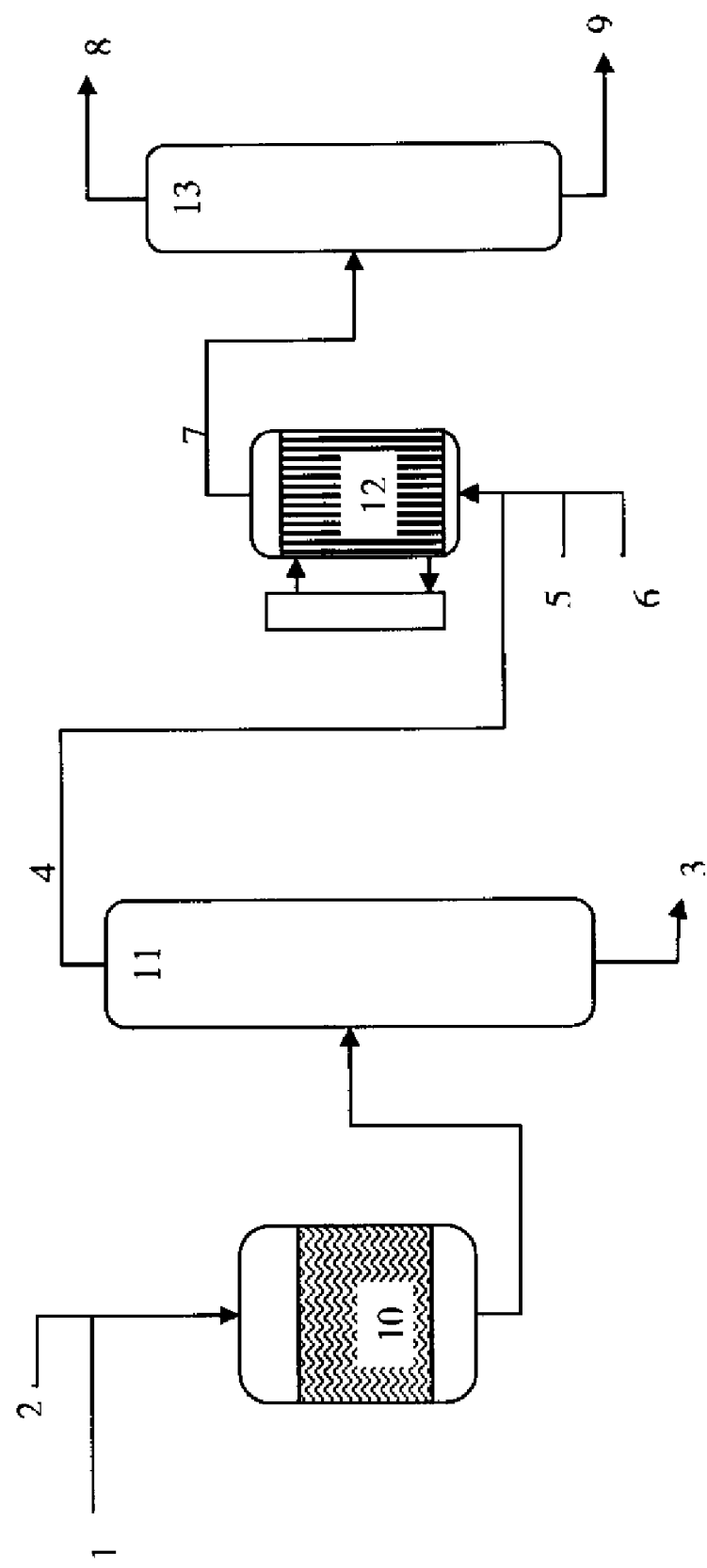
FIG. 1 is a schematic illustration of a preferred embodiment of the invention.

With reference to FIG. 1, the glycerol is introduced (1), into a first dehydration reactor (10). Molecular oxygen (2) can also be introduced, for example in the form of air or in the form of air enriched with or depleted of molecular oxygen. Preferably, the quantity of oxygen selected should be outside the inflammability range at any point of the installation. The presence of oxygen serves to limit the deactivation of the dehydration catalyst by coking. Moreover, the addition of oxygen improves the yield of the reaction for numerous catalyst systems.

The dehydration reaction is carried out in the gas phase in the reactor (10) in the presence of a catalyst at a temperature of between 150° C. and 500° C., preferably between 250° C. and 350° C., and at a pressure of between 1 and 5 bar, preferably between 1 and 3 bar.

The reactor (10) may operate in a fixed bed, fluidized bed or moving fluidized bed, or in a modular configuration (trays or baskets), generally in the presence of solid acidic catalysts.

The appropriate catalysts are homogeneous or multiphase materials, insoluble in the reaction medium, which have a Hammett acidity, denoted $H_0$, lower than +2. As indicated in U.S. Pat. No. 5,387,720, which refers to the article by K. Tanabe et al. in "Studies in Surface Science and Catalysis", Vol 51, 1989, chap 1 and 2, the Hammett acidity is determined by amine titration using indicators or by adsorption of a base in the gas phase. The catalysts meeting the acidity $H_0$ requirement lower than +2 can be selected from natural siliceous or synthetic materials or acidic zeolites; mineral supports, such as oxides, covered by inorganic acids, mono, di, tri or polyacids; oxides or mixed oxides, or heteropolyacids.

Advantageously, the catalysts are selected from zeolites, Neon® composites (based on sulphonic acid of fluorinated polymers), chlorinated aluminas, acids and salts of phosphotungstic and/or silicotungstic acids, iron phosphates doped with metals or alkali or alkaline-earth metals $FeP_xM'_yM''_yO_z$, and various solids of the metal oxide type such as tantalum oxide $Ta_2O_5$, niobium oxide $Nb_2O_5$, alumina $Al_2O_3$, titanium dioxide $TiO_2$, zirconia $ZrO_2$, tin oxide $SnO_2$, silica $SiO_2$ or alumino silicate $Al_2O_3$—$SiO_2$, impregnated with acidic functions such as borate $BO_3$, sulphate $SO_4$, tungstate $WO_3$, phosphate $PO_4$, silicate $SiO_2$, or molybdate $MoO_3$. According to the data in the literature, these catalysts all have a Hammett acidity $H_0$ lower than +2.

The preferred catalysts are sulphate zirconias, phosphate zirconias, tungstate zirconias, silicate zirconias, sulphate titanium or tin oxides, phosphate aluminas or silicas.

These catalysts all have a Hammett acidity $H_0$ lower than +2, and the acidity $H_0$ may vary to a wide extent, up to values as high as −20 in the reference scale with the Hammett indicators. The table given on page 71 of the publication on acid-base catalysis (C. Marcilly) Vol 1 published by Editions Technip (ISBN No. 2-7108-0841-2) illustrates examples of solid catalysts in this acidity range.

The gas stream leaving the reactor (10) consists of a mixture comprising acrolein, water, unconverted glycerol and by-products, such as hydroxypropanone, propanaldehyde, acetaldehyde, acetone, phenol, acrolein to glycerol addition products, glycerol polycondensation products, cyclic or non-cyclic glycerol ethers.

According to the inventive method, this stream is sent to a condensation unit (11), which separates a water-rich mixture (3) on the one hand, containing the heavy by-products such as phenol, hydroxypropanone, and the acrolein to glycerol addition products (acetals), glycerol polycondensation products, cyclic or non-cyclic glycerol ethers, propionic acid, acrylic acid, acetic acid, and, on the other, an acrolein-rich stream (4) containing the light by-products, such as acetaldehyde, propanaldehyde, acetone and possibly inert gases, CO and $CO_2$.

The partial condensation unit (11) may be an absorption column optionally coupled to an evaporator, a heat exchanger, a condenser, a dephlegmator, and any apparatus well known to a person skilled in the art, serving to carry out a partial condensation of an aqueous stream. The unit (11) may furthermore be used to heat the aqueous glycerol solution (1) fed to the reactor (10), thereby optimizing the energy cost of the installation.

The stream (3) is sent in full or in part either to a rectification or stripping column to recover the light fraction which could be absorbed in this stream, or to a wastewater treatment station. It may also be sent to a thermal oxidizer, or part of this stream can be recycled to dilute the glycerol to the desired concentration.

The acrolein-rich stream (4), stripped of the heavy by-products and most of the water, is sent to the oxidation reactor (12) where the acrolein can then be oxidized to acrylic acid with a controlled and higher acrolein partial pressure. The productivity of the reactor is thereby improved.

The reaction is carried out in the presence of molecular oxygen (6) which may be in the form of air or in the form of air enriched with or depleted of molecular oxygen, having a content of between 3 and 20% by volume, with regard to the incoming stream, and optionally in the presence of inert gases (5), such as $N_2$, $CO_2$, methane, ethane, propane or other light alkanes. The inert gases necessary for the method may optionally consist in full or in part of gases (8) obtained at the top of the absorption column (13).

The oxidation reaction takes place at a temperature of between 200° C. and 350° C., preferably from 250° C. to 320° C., and under a pressure of between 1 and 5 bar.

The reactor (12) can operate in a fixed bed, fluidized bed or moving fluidized bed. It is also possible to use a tray-type heat exchanger with a modular arrangement of the catalyst as described in documents EP 995491, EP 1147807 or US 2005/0020851.

All types of catalysts well known to a person skilled in the art can be used as oxidation catalyst for this reaction. In general, use is made of solids containing at least one element selected from Mo, V, W, Re, Cr, Mn, Fe, Co, Ni, Cu, Zn, Sn, Te, Sb, Bi, Pt, Pd, Ru, Rh, present in metal form or in oxide, sulphate or phosphate form. In particular, use is made of formulations containing Mo and/or V and/or W and/or Cu and/or Sb and/or Fe as main components.

The effluent (7) from the oxidation step, rich in acrylic acid, is then purified in a separation unit (13) to separate the light reaction products (8) on the one hand, such as propanaldehyde, acetaldehyde, acetone, CO and $CO_2$, inert diluting gases and unconverted acrolein, and, on the other, acrylic acid (9) which may still contain traces of heavy by-products.

The method according to the invention, even though it requires an additional unit associated with the intermediate step, has the advantage of using an economical raw material and of being able to optimize the two reaction stages separately. This increases the acrylic acid productivity and selectivity. The method remains demonstrably economical.

In comparison with a conventional method for preparing acrylic acid by catalytic oxidation of propylene, the method according to the invention serves to increase the acrylic acid productivity, while reducing the dependence on a fossil resource such as propylene. Such a method meets the criteria associated with the new concept of "green chemistry" in a more comprehensive framework of sustainable development.

EXAMPLES

A simulation using the ASPEN software was used to illustrate the method according to the invention. The percentages are expressed as mass %. Species present in a content lower than 1% are ignored.

Example 1

Figure 2:
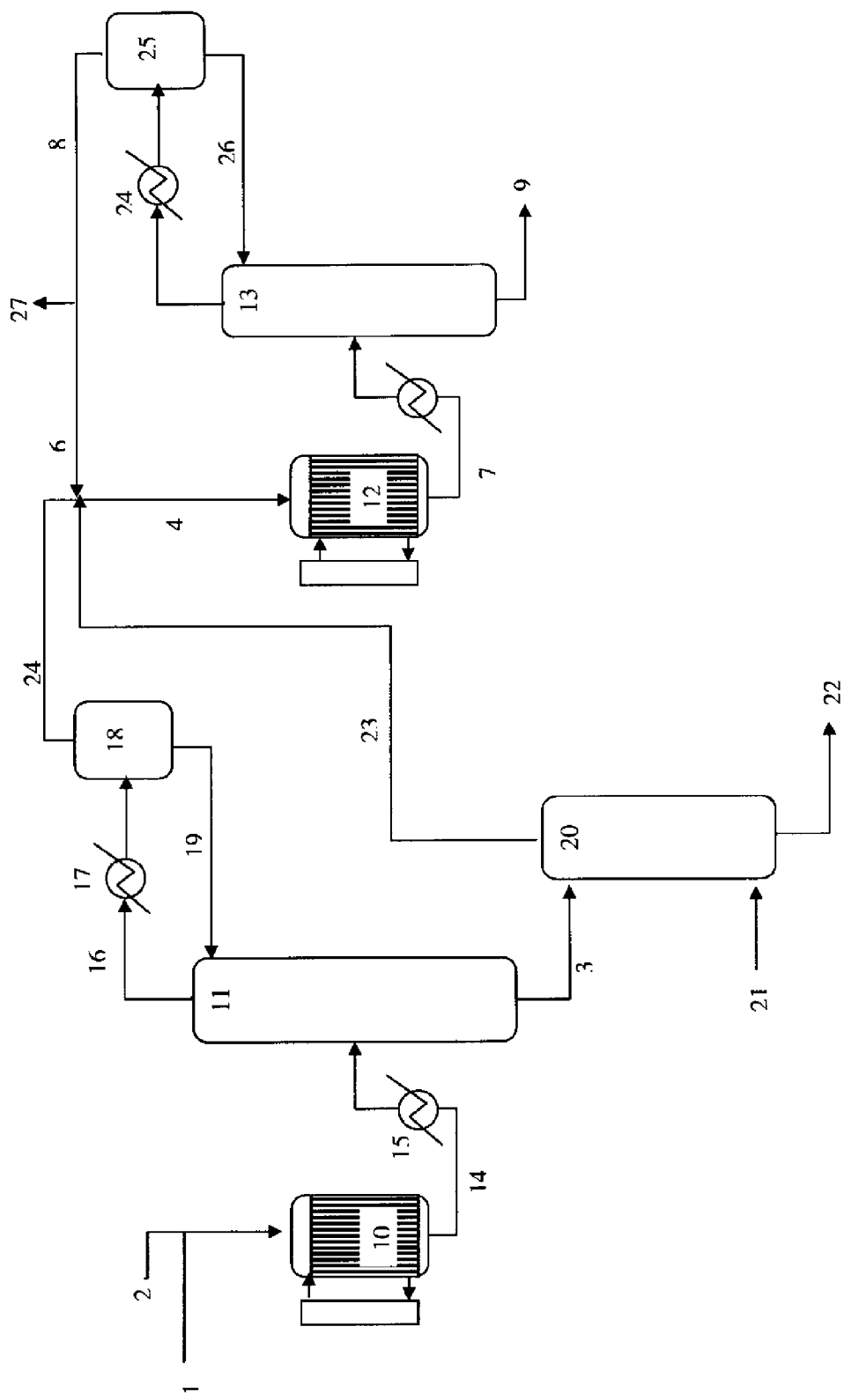
FIG. 2 is a schematic illustration of the preferred embodiment described in Example 1.

With Reference to FIG. 2

A gas stream at 331° C. under 2.0 bar (50.3 t/h, 34.5% glycerol, 34.5% water, 23.7% nitrogen, 7.2% oxygen) is sent to a multitube fixed bed reactor (10) containing a heterogeneous dehydration catalyst coupled with a molten salt bath. A gas stream (14) leaves this reactor at 320° C. under 1.7 bar (50.3 t/h, 47.9% water, 23.7% nitrogen, 5.0% oxygen, 16.4% acrolein, 1.6% acetaldehyde, 1.4% CO, 1.1% $CO_2$). This stream is cooled to 151° C. in a heat exchanger (15) and sent to the bottom of an absorption column (11) which comprises four theoretical stages. The gas stream (16) leaving the top of this absorption column at 102° C. is sent to a partial condenser (17) which cools it to 79° C., and then to a flash pot (18) which separates the gas phase (24) from the liquid phase (19). This liquid phase (19) is sent to the top of the absorption column (11). A liquid phase (3) is drawn off from the bottom of the absorption column, at 103° C. (20.4 t/h, 94.3% water, 1.4% acetic acid, 1.0% formic acid). This liquid phase (3) is sent to the top of a stripping column (20) comprising 8 trays, into which 4.4 t/h of air (21) is injected at the bottom at 90° C. under 1.7 bar. An aqueous stream (22) is recovered from the bottom of this stripping column (55° C., 18.6 t/h, 94.5% water, 1.3% acetic acid, 1.0% formic acid). The gas stream (23) recovered at the top of the stripping column is mixed with the gas phase (24) from the flash pot previously described (79° C., 29.9 t/h, 39.9% $N_2$, 27.2% acrolein, 8.4% oxygen, 16.2% water, 2.7% acetaldehyde, 2.4% carbon monoxide, 1.8% carbon dioxide) and with a gas stream (6) (33.5 t/h, 77.2% nitrogen, 3.6% oxygen, 7.2% water, 5.4% carbon dioxide, 4.5% carbon monoxide). The mixture is heated to 160° C., and then injected into a second multitube reactor (12) comprising an oxidation catalyst. At the outlet of this reactor, a gas stream (7) is obtained at 245° C. under 1.4 bar (69.6 t/h, 59.1% nitrogen, 13.1% water, 14.7% acrylic acid, 2.8% oxygen, 4.2% carbon dioxide, 3.4% carbon monoxide, 1.6% acetic acid). This stream is cooled to 157° C. and then injected at the bottom of the absorption column (13). At the top of this column, the gas stream is partially condensed in the heat exchanger (24), and then sent to a separator pot (25) which produces a liquid phase (26) and a gas phase (8) (55.6 t/h, 53° C., 77.2% nitrogen, 3.6% oxygen, 7.2% water, 5.4% carbon dioxide, 4.5% carbon monoxide). The liquid phase is returned to the column (13). The gas phase is partially recycled upstream of the reactor (12) via the stream (6). At the bottom of the absorption column (13), a stream (9) of concentrated acrylic acid is obtained (15.6 t/h, 64.1% acrylic acid, 34.4% water).

It may be observed that the method serves to remove certain impurities produced in the dehydration reactor (10) in the aqueous phase (22): for example, the hydroxypropanone and acetic acid flows in the gas stream leaving the dehydration reactor (10) are respectively 83.7 and 254 kg/h. They are 82.2 and 237 kg/h in the aqueous stream (22) from the bottom of the stripping column and 1.5 and 18 kg/h at the inlet of the oxidation reactor (12).

The invention claimed is:
1. A method for preparing acrylic acid from an aqueous glycerol solution, comprising the steps of:
dehydrating the glycerol to acrolein, in the gas phase in the presence of a catalyst having a Hammett acidity lower than +2 and under a pressure ranging from 1 to 5 bar,
partially condensing water and heavy by-products issuing from the dehydration step to yield purified acrolein in the gas phase; and
oxidizing the acrolein in the gas phase to acrylic acid.

2. The method of claim 1, wherein the aqueous glycerol solution has a concentration ranging from 20% to 99% by weight.

3. The method of claim 1, wherein the aqueous glycerol solution has a concentration ranging from 30% to 80% by weight.

4. The method of claim 1, further comprising adding molecular oxygen in the glycerol dehydration step.

5. The method of claim 4, wherein the aqueous glycerol solution has a concentration ranging from 20% to 99% by weight.

6. The method of claim 4, wherein the aqueous glycerol solution has a concentration ranging from 30% to 80% by weight.

7. A method for preparing acrylic acid from an aqueous glycerol solution, comprising the steps of:

dehydrating the glycerol to acrolein, in the gas phase in the presence of a catalyst having a Hammett acidity lower than +2 and under a pressure sufficient to dehydrate said glycerol to acrolein, partially condensing water and heavy by-products issuing from the dehydration step to yield purified acrolein in the gas phase; and oxidizing the acrolein in the gas phase to acrylic acid.

* * * * *